US009416086B2

(12) United States Patent
Barron et al.

(10) Patent No.: US 9,416,086 B2
(45) Date of Patent: Aug. 16, 2016

(54) PROCESSES FOR PURIFICATION OF ACID SOLUTIONS

(75) Inventors: Jerry Allan Barron, Gray, TN (US); Brandon Tyler Earls, Kingsport, TN (US); Carl Franklin Fillers, Greeneville, TN (US); Robert Sterling Kline, Kingsport, TN (US); Gregory Abbott Wellman, Jr., Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 288 days.

(21) Appl. No.: 12/982,150

(22) Filed: Dec. 30, 2010

(65) Prior Publication Data

US 2012/0123160 A1    May 17, 2012

Related U.S. Application Data

(60) Provisional application No. 61/413,234, filed on Nov. 12, 2010.

(51) Int. Cl.
*C07C 51/44* (2006.01)
*C07C 53/08* (2006.01)
*C07C 51/087* (2006.01)

(52) U.S. Cl.
CPC ............. *C07C 51/087* (2013.01); *C07C 51/44* (2013.01)

(58) Field of Classification Search
CPC ............................ C07C 51/087; C07C 51/44
See application file for complete search history.

(56) References Cited

U.S. PATENT DOCUMENTS

| | | | | |
|---|---|---|---|---|
| 3,125,551 A | * | 3/1964 | Punderson | 525/400 |
| 5,175,362 A | * | 12/1992 | Fillers et al. | 562/607 |
| 5,380,929 A | | 1/1995 | Erpenbach et al. | |
| 6,130,355 A | | 10/2000 | Jones | |
| 6,992,212 B2 | | 1/2006 | Zehner et al. | |

FOREIGN PATENT DOCUMENTS

| | | | |
|---|---|---|---|
| DE | 24 23 079 | | 11/1975 |
| DE | 24 23 079 A1 | | 11/1975 |
| DE | 2423079 A1 | * | 11/1975 |
| EP | 0087087 A1 | * | 2/1983 |
| EP | 0 087 870 A1 | | 9/1983 |
| JP | 48-30254 | | 8/1973 |
| JP | 48-302504 | * | 9/1973 |

OTHER PUBLICATIONS

Sloley, Distillation Column Design: Packing. In Encyclopedia of Chemical Processing. Taylor and Francis: New York, Published online: Dec. 12, 2007, pp. 729-748.*
Notification of Transmittal of the International Search Report and the Written Opinion of the International Searching Authority, or the Declaration date of mailing May 23, 2012 received in corresponding International Application No. PCT/US2011/057785.
Davis, Kenneth R. and Hogg, John L.; "Transition-State Structures for the Hydrolysis of Cyclic and Acyclic Carboxylic Acid Anhydrides"; Journal Organic Chemistry; 1983, vol. 48, No. 7, pp. 1041-1047.
Haldar, Raghunath and Rao, D. Phaneswara; "Experimental studies on limit cycle behavior of the sulphuric and catalzed hydrolysis of acetic anhydride in a CSTR"; Chemical Engineering Science, vol. 49, No. 4, 1991, pp. 1197-1200.
Janssen, H. J. et al.; "Hydrolysis of Acetic Anhydride in Concentrated Acetic Acid without Catalysis"; Industrial and Engineering Chemistry, vol. 49, No. 2, Feb. 1957, pp. 197-201.
Koskikallio, Jouko; "Kinetics of the Acid-Catalysed Solvolysis of Acetic Anhydride in Methanol-Water Mixtures"; Acta Chemica Scandinavica, 13, 1959, pp. 671-676.
Koskikallio, J. et al.; "Pressure Effect and Mechanism in Acid Catalysis"; Can. J. Chem., vol. 37, 1959, pp. 1360-1366.
Yvernault, Theophile; "Acid Catalysis of the hydrolysis of acetic anhydride in acetic acid"; Compt. Rend, 1955, 241, pp. 485-487 (abstract and original language).

* cited by examiner

*Primary Examiner* — Paul A Zucker
(74) *Attorney, Agent, or Firm* — James Arnold, Jr.

(57) ABSTRACT

The invention provides processes for purification of streams containing carboxylic acids and carboxylic acid anhydrides without using the amount of high-cost, corrosion resistant alloy required for a distillation column. The invention provides methods in which streams containing carboxylic acids and carboxylic acid anhydrides are subjected to a hydrolysis process by combining them with a stoichiometric excess of water and optionally an added hydrolysis catalyst. The resulting hydrolyzed stream is subsequently separated to produce a stream containing carboxylic acid and water and a carboxylic acid product stream comprising carboxylic acid.

42 Claims, No Drawings

PROCESSES FOR PURIFICATION OF ACID SOLUTIONS

CROSS-REFERENCE TO RELATED APPLICATION

This application claims priority to U.S. Provisional Application Ser. No. 61/413,234, filed Nov. 12, 2010, the disclosure of which is incorporated herein by reference in its entirety.

BACKGROUND OF THE INVENTION

Carboxylic acids and their anhydrides are widely produced and used in the chemical industry. Streams containing mixtures of a carboxylic acid and its corresponding carboxylic acid anhydride are common. Carboxylic acid anhydrides are used in many esterification processes that result in the formation of the carboxylic acid, so many esterification processes yield carboxylic acid solutions containing small concentrations of the corresponding anhydride of the carboxylic acid. Further, many manufacturing processes that produce carboxylic acid anhydrides result in such streams. Some examples include product refining activities associated with processes for carbonylation of methyl acetate, dimethyl ether, or both, (whether alone or with methanol), as well as processes that involve carbonylation of methyl acetate or dimethyl ether and subsequent reaction of some or all of the resulting acetic acid anhydride with methanol.

Purification of carboxylic acid solutions that contain their corresponding acid anhydrides is challenging because of the difficulty and expense of obtaining pure materials through distillation and because of publications indicating that dilute mixtures of some anhydrides in their corresponding carboxylic acids are significantly more corrosive than either pure carboxylic acid or solutions that contain higher concentrations of the carboxylic acid anhydride in acid. As a result, one designing separation equipment such as a distillation column to fractionate such products would tend to select specialized, corrosion-resistant alloys to address distillation mixtures having more corrosive compositions. However, such a column would involve significantly higher costs due to the costs of such alloys.

Furthermore, sales specifications for some carboxylic acids require that the carboxylic acid be slightly aqueous, that is, that water would be the highest concentration impurity present in the carboxylic acid. Conventional distillation of a mixture of carboxylic acid and the corresponding carboxylic acid anhydride would result in an anhydrous rather than aqueous distillate product because the highest concentration impurity present would be the carboxylic acid anhydride rather than water. Thus, it would be advantageous to convert such streams from anhydrous to aqueous.

It would thus be desirable to develop alternative processes for purification of streams containing carboxylic acids and carboxylic acid anhydrides without using the amount of high-cost, corrosion-resistant alloy required for a distillation column, membrane or other equipment intensive separation process to which produces the substantially pure carboxylic acid. It would also be advantageous to provide a process that yields an aqueous carboxylic acid product.

BRIEF SUMMARY OF THE INVENTION

The invention provides processes for purification of streams containing carboxylic acids and carboxylic acid anhydrides without using the amount of high-cost, corrosion resistant alloy required for a distillation column. or other equipment intensive separation process. The invention provides methods in which streams containing carboxylic acids and carboxylic acid anhydrides are subjected to a hydrolysis process by combining them with a stoichiometric excess of water and optionally an added hydrolysis catalyst. The resulting hydrolyzed stream is subsequently separated to produce a separated stream containing carboxylic acid and water and a carboxylic acid product stream containing carboxylic acid.

In some embodiments, the method further includes recycling the stream containing carboxylic acid and water to the hydrolysis zone. Where the separation is a distillation process, for example, this stream can be the distillation overhead or a sidedraw. This provides the additional benefits of returning the carboxylic acid contained in the separated stream to the process and using the water more efficiently. Where the recycled stream is cooled, such as through a condensation step, the introduction of the cooled recycled material to the hydrolysis zone also provides thermal ballast because the introduction of additional mass into the hydrolysis zone moderates the temperature rise imparted to the process by the exothermic hydrolysis reaction. This moderation of temperature rise can provide longer catalyst life for certain hydrolysis catalysts.

In some embodiments, the process includes a cooling process in which cooling is applied to the hydrolysis zone itself, one or more feeds to the hydrolysis zone, or both. This cooling process is intended to offset in part the exothermic nature of carboxylic acid anhydride hydrolysis reactions and the desire to maintain sufficiently low temperatures for catalyst protection or suppression of vaporization.

DETAILED DESCRIPTION

The invention provides methods for purification of carboxylic acid streams that also contain at least one carboxylic acid anhydride. The invention provides methods in which streams containing carboxylic acids and carboxylic acid anhydrides are subjected to a hydrolysis process by combining them with a stoichiometric excess of water and optionally an added hydrolysis catalyst. The resulting hydrolyzed stream is subsequently separated to produce a separated stream containing carboxylic acid and water and a product stream containing carboxylic acid. The product stream may also contain low concentrations of water, resulting in an aqueous product stream. This separation step allows reduction of excess water in the product stream. The method also allows conversion of an anhydrous carboxylic acid stream (in which the anhydride is the impurity having the highest or one of the highest concentrations) to an aqueous stream (in which the water is the impurity having the highest concentration or one of the highest concentrations). The use of a hydrolysis process also reduces the need for use of higher cost corrosion resistant alloys in distillation or other separation equipment. The use of a separation process after the hydrolysis allows separation of excess water from the acetic acid product stream. By providing an opportunity to remove excess water after hydrolysis, this approach allows the hydrolysis process to operate with a wide arrays of degree of stoichiometric excess of water to anhydride, thus reducing the need for costly and difficult control systems regarding the feed rate of water to the hydrolysis process.

In some embodiments, the method further includes recycling the separated stream to the hydrolysis zone. This provides the additional benefits of returning the carboxylic acid contained in the separated stream to the process and using the water more efficiently. In some embodiments, the reuse of this water via the acid-rich separated product creates the potential to enhance the efficacy of process quality control, for reasons explained below. Where the separated stream is cooled, for example through condensation of a vapor stream, the introduction of the recycled material also provides a significant volume of cooled material in the hydrolysis zone to offset the heat generated by the exothermic hydrolysis process.

As used throughout this application, percent concentrations are based on total weight of the composition except where expressly stated otherwise.

Streams Containing a Carboxylic Acid and a Carboxylic Acid Anhydride

The stream fed to the hydrolysis process contains a carboxylic acid and the anhydride of that carboxylic acid. The stream contains more than 0% carboxylic acid but contains less than 100% carboxylic acid. In some embodiments, the ratio of carboxylic acid to carboxylic acid anhydride is at least about 80:10 but less than 100% carboxylic acid. The stream may contain other components as well, such as impurities from the source process that may or may not react with water.

The hydrolysis feed stream may also be selected from streams having a variety of lower ends of the carboxylic acid concentration ranges, including greater than 0, at least about 5, at least about 10, at least about 25, at least about 40, at least about 60, at least about 85, at least about 90, at least about 92.5, at least about 95, or at least about 97.5% percent, but in all cases less than 100 percent. The upper end of any of the foregoing carboxylic acid concentration ranges may also be a variety of numbers, including about 75, about 80, about 85, about 90, about 95, about 96, about 97, about 98, about 99 or about 99.5%. Thus, a variety of ranges of concentrations may be fed to the process, such as between about 80% and about 99.5%, between about 80% and about 85%, between about 80% and about 95%, between about 85% and about 96%, between about 92.5% and about 95%, between about 95% and about 99%, between about 90% and about 96%, between about 92.5% and about 96%, between about 92.5% and about 95%, between about 92.5% and about 97%, between about 90% and about 95%, between about 90% and about 99%, and so on.

The stream further contains the anhydride of the carboxylic acid. The anhydride is present in a concentration of at least about 0.01%. In some embodiments, the carboxylic acid and carboxylic acid anhydride account for about 100% of the total composition. In some embodiments, other components account for at least about 1% of the total composition. Depending on its source, the stream may have a variety of ranges of ratios of parts of carboxylic acid to carboxylic acid anhydride. Some examples include about 0.5:99.5 to about 99.5:0.5, about 10:90 to about 95:5, about 25:75 to about 50:50, about 5:95 to about 50:50, about 25:75 to about 75:25, about 40:60 to about 60:40, about 60:40 to about 99.5:0.5, about 70:30 to about 99.5:0.5, about 80:20 to about 90:10, about 80:20 to about 99.5:0.5, about 75:25 to about 95:5, about 75:25 to about 85:15, about 85:15 to about 95:5, about 90:10 to about 95:5, about 90:10 to about 97:3, greater than about 90%, greater than about 95%, greater than about 97%, greater than about 80%, and so on. Other components may be present in the feed to the hydrolysis process, and the identity and amount will of course depend on the source of the stream. Some examples of components that may be present include acetone, methyl acetate, other carboxylic acids, other anhydrides, ethylidene diacetate, iodine, iodine containing compounds, and other process-derived impurities such as compounds extracted during acetylation of cellulose or wood. In some embodiments, the total amount of components other than the carboxylic acid and carboxylic acid anhydride are no greater than about 0.1%. In some embodiments, the total amount of components other than the carboxylic acid and carboxylic acid anhydride are less than about 1%.

As used throughout this application, the "stream" fed to the hydrolysis process refers to the total amount of material fed to the hydrolysis process, excluding any recycle stream (if present) from the separation process and from any water source. Thus, in embodiments where there are two or more streams fed to the hydrolysis process (whether by combining the streams first or by feeding them simultaneous to equipment in which the hydrolysis occurs) the percentages of acid and anhydride above refer to percentages the total amount of material in those streams (again, excluding any recycle stream from a downstream separation process and water feeds). For example, in some embodiments, the stream fed to the hydrolysis zone includes a stream containing at least about 90% carboxylic acid and another stream containing at least about 90% of a carboxylic acid anhydride. Such multiple streams can combined prior to, simultaneous with, or after at least one of such solutions is combined with the stoichiometric excess of water and, optionally, recycled streams.

In some embodiments, the carboxylic acid is selected from formic acid, acetic acid, propionic acid, butyric acid, isobutyric acid and combinations of one or more of the foregoing. In some embodiments, the carboxylic acid is acetic acid. The carboxylic acid anhydride is the anhydride that corresponds to the carboxylic acid in the composition. As used throughout this application, "the anhydride of the carboxylic acid" or "corresponding anhydride" in reference to a carboxylic acid refers to the fact that the anhydride is a symmetrical acid anhydride on which both acyl groups are the same acyl groups that would be derived from the referenced carboxylic acid. Thus, the "corresponding anhydride" to acetic acid is acetic anhydride. However, the foregoing does not preclude applicability of the invention to mixtures containing more than one type of carboxylic acid, more than one type of carboxylic acid anhydride, or both. Furthermore, the invention is not limited to streams that contain only symmetrical acid anhydrides and the feed streams may also contain one or more asymmetrical or "mixed" acid anhydrides in addition to the corresponding anhydride.

The stream(s) fed to the hydrolysis process may be derived from any source or combination of sources, including any of a variety of processes, such as manufacturing or purification processes. Some examples of such manufacturing processes include processes for manufacturing acetic anhydride or blends of acetic acid and acetic anhydride, esterification processes, and substitution reaction processes in which a carboxylic acid anhydride is reacted with a different carboxylic acid to produce a composition containing the anhydride of the different carboxylic acid (for example, reacting acetic anhydride with propionic or a butyric acid to produce acetic acid and propionic or butyric anhydride). Some examples of anhydride (or anhydride/acid) manufacturing processes include processes that manufacture of acetic anhydride through carbonylation of methyl acetate, dimethyl ether, or both (with or without subsequent processes to react of some or all of the resulting acetic anhydride with methanol or coproduction of acetic acid through simultaneous carbonylation of methanol. Some examples of esterification processes include acetylation or esterification of cellulose or wood, and acetylation or other esterification processes used in the food, fragrance, or pharmaceutical manufacture (e.g., acetylsalicylic acid, acetaminophen, sucralose, aspartame, etc.). Some examples of purification processes include separation processes that partially fractionate a carboxylic acid and the corresponding carboxylic acid anhydride. For example, the stream can include an overhead or sidedraw from a distillation process that partially fractionates a carboxylic acid and a carboxylic acid anhydride, but avoids creating carboxylic acid streams that contain undesirably low carboxylic acid anhydride concentrations. In some embodiments, the stream can include the product stream from a flash process associated with (i.e. downstream from) a carbonylation process, wherein the flash process is used to separate product streams from high boiling materials such as carbonylation catalyst and other impurities.

As noted above, in some embodiments, the stream fed to the hydrolysis process includes one or more streams that contain one or more asymmetrical "mixed anhydrides", such as, for example acetic propionic anhydride or propionic isobutyric anhydride. The invention provides an method to convert each such mixed anhydride into two molecules of different types of carboxylic acids (for example, a mole of acetic propionic anhydride would be converted to one mole each of acetic acid and propionic acid).

In some embodiments, the hydrolysis feed stream is a purified carboxylic acid anhydride stream. Other potential hydrolysis feed streams include crude carboxylic acid streams (with carboxylic acid anhydride as the primary impurity) or crude carboxylic acid anhydride streams (with carboxylic acid as the primary impurity). Still other potential hydrolysis feed streams include streams sourced from processes which utilize a carboxylic acid anhydride as a feedstock.

Streams may have been previously treated prior to hydrolysis, for example by having impurities removed, (e.g. iodine compounds from a carbonylation reactor, wood-derived impurities in a byproduct from wood esterification processes, etc.) or by having the anhydride concentration partially reduced by other processes, thus reducing or minimizing the amount of hydrolysis required. Examples of such other processes include, for example, distillation or other processes to separate a portion of the anhydride from the stream.

The temperature can be any effective and suitable temperature. In some embodiments, the temperature of the reactant mixture in the hydrolysis process is between about 20 and about 100° C. In some embodiments, the temperature of the reactant mixture in the hydrolysis process is between about 20 and about 50° C. In some embodiments, the temperature is between about 55 and about 80° C. In some embodiments, the temperature is between about 30 and about 75° C. In some embodiments, the temperature is between about 55 and about 65° C. In some embodiments, the temperature is between about 65 and about 75° C. In some embodiments in which an added hydrolysis catalyst is used, the temperature is maintained below levels that will unacceptably degrade the catalyst.

In embodiments in which the feed to the hydrolysis zone actually contains multiple streams, the streams may have similar or dissimilar compositions, and may have similar or dissimilar sources. In some embodiments, the feed includes both a dilute stream of carboxylic acid anhydride in the carboxylic acid, and an anhydride-rich stream added to adjust a facility's overall relative production of carboxylic acid and carboxylic acid anhydride. This may be useful, for example, for a coproduction facility that makes both acetic acid and acetic acid anhydride. Some examples of other streams that can be part of the feed include one or more of the following: an acid-rich overhead stream or sidedraw from an anhydride purification column; acetyl byproducts from the production of diketene derivatives; acetyl byproducts from the acetylation processes (e.g., acetylating cellulose or lignocellulosic material). Where an anhydride-rich stream is included, that stream may contain, for example, at least about 50% of a carboxylic acid anhydride or other concentrations (e.g. at least about 60%, at least about 75%, at least about 90%, or ranges such as about 50% to about 75%, about 75% to about 85%, about 85% to about 95%, and about 90% to about 100%.)

Hydrolysis

The stream is subjected to hydrolysis by placing it in at least one hydrolysis zone with a stoichiometric excess of water and optionally an added hydrolysis catalyst. The water source is not critical and any suitable feed stream that contains a stoichiometric excess of water may be used. The invention is not limited to embodiments in which a single stream containing water is fed to the hydrolysis zone. In some embodiments, multiple sources of water are fed to the hydrolysis zone.

As used throughout this application, "stoichiometric excess of water" means more moles of water than the number of moles of carboxylic acid anhydride. In the hydrolysis process, a single molecule of water reacts with a given molecule of carboxylic acid anhydride to provide two molecules of carboxylic acid. More moles of water than carboxylic acid anhydride provides a stoichiometric excess. Thus, in a batch process, a greater number of moles of water are combined in the batch than the number of moles of carboxylic acid anhydride. In a continuous process, a greater number of moles of water per unit of time are fed to the hydrolysis zone than the number of moles of carboxylic acid anhydride fed during the same period.

The ratio of water to anhydride added to the hydrolysis process is not limiting, and may be tightened or relaxed based on the amount of water in the resulting hydrolyzed stream that is considered acceptable. In some embodiments, the ratio of water to anhydride fed to the hydrolysis process is between about 1.05:1 and about 10:1. In some embodiments, the ratio of water to anhydride fed to the hydrolysis process is between about 3:1 and about 10:1. In some embodiments, ratio of water to anhydride fed to the hydrolysis process is between about 1.05:1 and about 1.4:1 (i.e. about 5% to about 40% molar excess of water). In some embodiments, the ratio of water to anhydride fed to the hydrolysis process is between about 1.05:1 and about 1.1:1 The downstream separation process in some embodiments allows the hydrolysis process to accommodate wide ranges of stoichiometric excess. Thus, in some embodiments, the stoichiometric ratio of water to carboxylic acid anhydride is selected as a value or range that is sufficiently low to allow downstream water-acid separation processes (e.g. distillation) to purify the carboxylic acid stream to a desired degree. In some embodiments involving use of an added hydrolysis catalyst, the degree of stoichiometric excess of water fed to the hydrolysis zone may be increased over time compensate for hydrolysis catalyst becoming spent or otherwise experiencing diminished efficacy with age or continued use.

Where used, the added hydrolysis catalyst may include one or more of any effective and otherwise suitable hydrolysis catalysts. Some criteria that may be considered in the selection of an appropriate catalyst are: the ability to catalyze the hydrolysis so as to cause it to occur at an acceptable rate; stability under the temperature and pressure used in the process; stability in the presence of the components of the stream being treated; and lifetime in process.

Where used, added hydrolysis catalysts may be present as liquids, solids, or both. Some examples of liquid catalysts include acids and bases such as sulfuric acid, phosphoric acid, hydrochloric acid, perchloric acid, sulfonic acids, pyridines (and various derivatives thereof), and cyclic or acyclic amines. In some embodiments, solid catalytic materials used as added hydrolysis catalysts incorporate one or more chemical functionalities of these liquid catalysts. Some examples of solid materials that may be used as added hydrolysis catalysts include resins, gels, zeolites, clays, aluminas, and silicas. Many of these materials can be modified either in physical form (e.g., structure, pore size, surface area, etc) or chemically (by addition of adsorbents, performing chemical exchange or chemical surface modifications, or moderation of either acidic or basic groups by any of these or other techniques). In some embodiments, the added hydrolysis catalyst is selected from a resin material. Some examples of such materials include certain AMBERLYST resins available from Rohm & Haas, Philadelphia, Pa., DOWEX 50 and DOWEX G26, available from Dow Chemical Company, Midland Mich. and PUROLITE C100H available from The Purolite Company, Bala Cynwyd, Pa. In some embodiments, the cation exchange material is a macroreticular polymeric cation exchange resin having the hydrogen form of a sulfonic acid. Examples of such resins include resins containing styrene divinylbenzene copolymers functionalized with sulfonic acid groups such as certain AMBERLYST resins, in particular AMBERLYST 15.

The amount of added hydrolysis catalyst used is not critical to the invention and any effective and desired amount may be added. Where used, the amount of added hydrolysis catalyst present within the hydrolysis zone will depend principally on the added hydrolysis catalyst employed, the flow rate and composition of the hydrolysis feed stream, the desired residence time in the catalyst area, and desired composition of the hydrolysis product stream. Where added hydrolysis catalyst resides in the hydrolysis zone for an extended period (e.g. a bed of solid catalyst used in a continuous process) an excess of catalyst may be charged to the bed initially to provide for continued effective catalysis as part of the added hydrolysis catalyst becomes spent or is otherwise experiences diminished efficacy with age or continued use.

Embodiments also exist in which the hydrolysis occurs without an added hydrolysis catalyst. In some embodiments, the decision about whether or not to use an added catalyst may depend upon what constitutes an acceptable rate of hydrolysis for the defined process. Carboxylic acids such as acetic acid or propionic acid present in the stream and produced in situ by the hydrolysis reaction is an example of an organic weak acid that may provide some catalysis in the absence of an added catalyst. Additionally, the use of elevated temperatures, pressures, or extended residence times may obviate the need to use an added catalyst to increase the rate of the hydrolysis reaction. Because of the weak catalysis performed by such carboxylic acid, the term "added hydrolysis catalyst" refers to a catalyst other than the carboxylic acid already present in the feed stream that is added to or otherwise contacted with the stream in the hydrolysis zone.

In some embodiments, the hydrolysis zone may include a first sub-zone that does not contain added hydrolysis catalyst and a second sub-zone that contains added hydrolysis catalyst. The configuration can be helpful, for example, in embodiments in which the feed to the hydrolysis process is rich in the anhydride because higher concentrations of anhydride have less need for added hydrolysis catalyst. In some embodiments, an initial hydrolysis sub-zone without added hydrolysis catalyst is used to reduce the anhydride concentration of a rich stream, and a second hydrolysis sub-zone with added hydrolysis catalyst is then used to further treat the lower concentrations of anhydride.

The location and configuration of the hydrolysis zone is not critical. The zone may be any type of location or containment that can be configured to catalyze the reaction, and if desired, remove desired amounts of heat generated by the hydrolysis reaction. Some examples include vessels, tanks, pipes and combinations of any of the foregoing. The size and configuration depends on the amount of carboxylic acid anhydride to be hydrolyzed. Where solid added hydrolysis catalyst is used, some examples of hydrolysis zone configurations include packed beds, packed pipes, and other equipment which can be used to cause contact of one or more liquid feed streams with the added hydrolysis catalyst. In some embodiments, the hydrolysis zone is a catalyst-packed bed. In some embodiments, the hydrolysis zone receives a mixed stream containing the hydrolysis feed stream and the water feed stream. The mixture enters the hydrolysis zone from the top, is distributed by a liquid distribution device, and flows in a downflow mode, flowing over the added hydrolysis catalyst and exiting the bottom of the hydrolysis zone. The hydrolysis feed stream, water feed stream, and any other streams may be fed to a vessel as separate streams or as part of a mixture that is first combined prior to introduction into the vessel. The hydrolysis zone may or may not include liquid distribution devices such as shower heads, spray nozzles, or liquid distribution trays. If fed separately, the hydrolysis feed stream and water feed stream may be fed co-currently or counter-currently. The stream or streams fed to the hydrolysis zone may flow in an upflow or downflow mode. Any effective material of construction may be used for the hydrolysis zone. In some embodiments, the hydrolysis zone is sufficiently corrosion-resistant for the range of compositions between the hydrolysis feed and the hydrolysis product. For example, in some embodiments for the hydrolysis of a stream of 95% acetic acid and 5% acetic acid anhydride, the hydrolysis zone is constructed of a high-nickel alloy such as Alloy C-276.

The design of the hydrolysis zone, including selection and sizing of equipment and selection and quantity of added hydrolysis catalyst can be readily determined based on literature data, standard engineering calculations, or mathematical models. The composition, volume and temperature of the hydrolysis feed stream should be considered. In some embodiments, a hydrolysis vessel design is based on the scale up of a pilot reactor described by a residence time of about 7.4 minutes and a superficial velocity of about 0.45 meters per minute.

The hydrolysis zone results in a hydrolyzed stream, in which at least some of the carboxylic acid anhydride molecules have been hydrolyzed to the corresponding carboxylic acid. In some embodiments, the anhydride content is less than about 1%. In some embodiments, the anhydride content is less than about 0.5%. In some embodiments, the anhydride content is below detectable limits. In some embodiments, the anhydride content is zero. The hydrolyzed stream also contains water due to the stoichiometric excess.

Optional Cooling

In some embodiments, the process further contains at least one cooling process or step. The cooling process cools one or more feeds to the hydrolysis zone, or the material within the hydrolysis zone. The cooling process can help to counteract the exotherm from the hydrolysis process, especially when higher concentrations of anhydride are included in overall the feed. This can be particularly beneficial, for example, when dealing with added hydrolysis catalysts that can degrade at elevated temperatures, but may be used in any configuration where cooling is desired.

Cooling takes place in a cooling zone, which may be include some or all of a hydrolysis zone, areas separate from a hydrolysis zone, or both. The location and configuration of the optional cooling zone is not critical and any desirable type of location or containment that can be configured to remove a heat can be used. Some examples include one or more shell-and-tube heat exchangers, one or more plate-and-frame heat exchangers, one or more double-pipe exchangers, or other equipment which transfers heat from the warm hydrolysis reaction mixture to a cool utility or process stream such as water, air, or other fluids. In some embodiments, the cooling zone may include a shell-and-tube heat exchanger. Some or all of the heat exchanging equipment in a cooling process may be deactivated in certain process scenarios, thus allowing the hydrolysis unit to process a variety of concentrations of carboxylic acid anhydride but allowing reduction or elimination of heat exchange operation when necessary. Cooling medium may be water or any other suitable coolant.

In some embodiments, one or more cooling process is combined with a hydrolysis zone, for example, by using a heat exchanger packed with solid hydrolysis catalyst. In some embodiments, the cooling process occurs in one or more separate cooling zones. Combinations may also be used, such as embodiments having a cooled hydrolysis zone and a cooling zone upstream of the hydrolysis zone. Any effective or desirable configurations of cooling processes and hydrolysis zones may be used. Some examples include arrangement of cooling zones in series or parallel upstream from the hydrolysis zone, one or more cooling zones followed by one or more hydrolysis zones arranged in series or parallel with the one or more cooling zones. In some embodiments, the process includes one shell-and-tube heat exchanger acting as a cooling zone and arranged in series directly upstream from one packed bed acting as a hydrolysis zone. The cooling process may also be configured to cool only one of the feeds to the hydrolysis zone, or a combination of feeds.

Separation

The hydrolyzed stream is further processed in a separation zone to separate at least some of the water from the carboxylic acid in the hydrolyzed stream. The separation results in a carboxylic acid product stream that has the desired level of purity and a separated stream containing carboxylic acid and water. Any effective separation zone may be used, including, for example, membrane processes and distillation processes. In some embodiments, the separation process is a distillation process in which the resulting carboxylic acid product stream taken from the underflow of the distillation process has the desired level of purity and the separated stream is taken from the overhead or a sidedraw. The equipment and parameters of the separation are not critical as any effective means of separating carboxylic acid from water may be used. Parameters will depend on the flow rate of hydrolyzed stream, amount of water contained in the hydrolyzed stream and level of purity desired in the final carboxylic acid product.

In some embodiments, the carboxylic acid product stream contains at least about 80% carboxylic acid. Embodiments also exist in which the carboxylic acid product stream contains at least about 85%, at least about 90%, at least about 95%, at least about 97%, at least about 98%, at least about 99%, at least about 99.5% carboxylic acid, at least about 99.75% carboxylic acid, or at least about 99.8% carboxylic acid. In some embodiments, the carboxylic acid product stream is a glacial acetic acid having an acid content of about 99.85%. In some embodiments, the carboxylic acid may contain some water and thus be an aqueous stream.

The separated stream will contain relative amounts of water and carboxylic acid that depend on the above parameters, and the amount of water in the hydrolyzed stream that is fed to the distillation zone. In some embodiments, the separated stream contains between about 0.5 and about 95% water. In some embodiments, the separated stream contains between about 0.5 and about 50% water. In some embodiments, the separated stream contains between about 0.5 and about 25% water. In some embodiments, the separated stream contains between about 0.5 and about 10% water. In some embodiments, the separated stream contains between about 10 and about 20% water. In some embodiments, the separated stream contains between about 25 and about 50% water. In some embodiments, the separated stream contains between about 25 and about 40% water. In some embodiments, the separated stream contains between about 40 and about 55% water. In some embodiments, the amount of water in the separated stream may increase over time, as increasing stoichiometric excess of water fed to the hydrolysis zone may compensate for added hydrolysis catalyst becoming spent or otherwise experiencing diminished efficacy with age.

Further Processing and Use of Streams

In some embodiments, the carboxylic acid product stream may be processed further. For example, the purity of the carboxylic acid in the product stream may be improved by further separation processes, such as membrane processes or distillation to remove impurities such as high-boiling compounds such as color bodies or corrosion metals. Any type of desired or useful additional processing may be used with the invention.

The separated stream from the separation zone may be disposed of or used in any useful manner. For example, such a stream may be used in any process where a dilute stream of carboxylic acid in water is useful. Some examples include use of dilute streams of acetic acid in water in processes for production of methyl acetate from methanol and acetic acid or in processes for production of acetic acid through hydrolysis of acetic anhydride.

In some embodiments, the separated water and acid stream from the separation zone is recycled to the hydrolysis zone of the process. Where the separated stream is a heated stream such as a distillation overhead or sidedraw, it can be chilled and condensed before recycling. Any standard means of condensation or chilling may be used. The stream may be recycled to the hydrolysis zone by introducing it directly to the hydrolysis zone or combining it with one or more feeds to the hydrolysis zone.

In some embodiments involving a recycle stream, the water levels in the recycle stream are measured, for example by using an in-stream monitor. Several such monitors and other means of measurement are commercially available, and any effective monitoring device suitable for the stream may be used. The monitor may measure the recycle stream itself or a feed line that includes the recycle stream combined with other feed components. This monitor can provide a feedback loop to indicate variation in the stoichiometric excess of water in the feed to the hydrolysis zone. As such, the feedback from the monitor may be used as a basis for controlling or adjusting the rate of fresh water added to the hydrolysis zone. This may be accomplished manually or through an automated control loop. In some embodiments, a decision is made about whether or not to adjust the feed rate of stoichiometric excess of water to the hydrolysis process based on the measurement of the water content in the separated stream and, if the decision is to adjust the flow rate, an adjustment of the flow rate is made in accordance with the decision. In some embodiments, the decision to adjust feed rate includes a decision as to the extent to which water feed rate needs to be adjusted, and the amount of adjustment is in accordance with the decision.

EXAMPLES

Example 1

A continuous stream containing 95% acetic acid and 5% acetic anhydride by weight and a temperature between 40 and 45° C. is fed at a flow rate of 109 parts per hour to a hydrolysis process. Parts per hour as described in this example are volumetric. The stream is fed by being combined with a demineralized water steam flowing at a rate of 1 part per hour and with a recycle stream (described below) in a pipe that feeds to the top of a hydrolysis vessel. The hydrolysis vessel is a simple reactor composed of Hastalloy C-276 and having a volume of 1747 volumetric parts (i.e. parts having the same volume as the volumetric component of the parts per hour feed). A heat exchanger for non-contact cooling with water of feeds to the vessel is available for this equipment, but was not used in this particular run. The vessel is single bed packed with AMBERLYST 15, a styrene divinylbenzene copolymer functionalized with sulfonic acid groups and available from Rohm & Haas, Philadelphia, Pa. The bed is sized and charged to provide a superficial residence time of 7.4 minutes for the stream.

A hydrolyzed stream from the underflow of the hydrolysis vessel containing 3% water in acetic acid is fed at a flow rate of 109 parts per hour to a distillation column constructed of 316L stainless steel. The distillation column has 35 trays, a reflux ratio of about 1.6 and a head temperature of about 109-110° C. and the material enters the column at tray 27. The underflow of the distillation column contains at least 99.8% acetic acid, and the overhead of the distillation column contains about 87% acetic acid and about 13% water. The overhead from the column is condensed to a temperature of 62° C. and is piped at a rate of 38 parts per hour to combine with the original feed stream containing acetic acid and acetic anhydride and the water stream, (as described above), so that the three streams are fed together to the hydrolysis vessel. The underflow is fed at a rate of 120 parts per hour to a second distillation column to separate corrosion metals and low boiling impurities from the product. This second column has 6 trays, a reflux ratio of approximately 0.5, and a head temperature of approximately 118° C., The material enters the column beneath the bottom tray. The final acetic acid product from the second distillation column is condensed and contains at least 99.8% acetic acid and less than 0.15% water.

In the specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method comprising:
    contacting at least one feed stream comprising a carboxylic acid and a carboxylic acid anhydride with a stoichiometric excess of water in a hydrolysis zone, thereby hydrolyzing at least some of the carboxylic acid anhydride wherein the hydrolysis zone is located in a containment, wherein the containment comprises a vessel packed with a solid hydrolysis catalyst, and wherein the at least one feed stream comprises at least about 40 percent carboxylic acid by weight,
    withdrawing a hydrolyzed stream comprising carboxylic acid and water from the hydrolysis zone, and
    processing at least some of the hydrolyzed stream in a separation zone that is not located in the containment to produce a separated stream comprising carboxylic acid and water and a product stream comprising carboxylic acid;
    wherein the method further comprises recycling at least some of the separated stream to the hydrolysis zone.
2. The method of claim 1, wherein the vessel comprises a bed or pipe packed with the solid hydrolysis catalyst.
3. The method of claim 2, wherein the vessel comprises a heat exchanger packed with the solid hydrolysis catalyst.
4. The method of claim 1, wherein the method further comprises generating a measurement of the water content of at least some of the separated stream it is recycled to the hydrolysis zone.
5. The method of claim 4, wherein the method further comprises making a decision about whether or not to adjust the flow rate of the stoichiometric excess of water fed to the hydrolysis zone based on the measurement of the water content and, if the decision is to adjust the flow rate, making an adjustment to the flow rate in accordance with the decision.
6. The method of claim 1, wherein the carboxylic acid is acetic acid and the carboxylic acid anhydride is acetic anhydride.
7. The method of claim 5, wherein the carboxylic acid is acetic acid and the carboxylic acid anhydride is acetic anhydride.
8. The method of claim 1, wherein the separation zone comprises a distillation zone, the separated stream comprises at least one distillation overhead or sidedraw from the distillation zone and the product stream comprises at least one distillation underflow from the distillation zone.
9. The method of claim 1, wherein the method further comprises cooling at least part of the hydrolysis zone, at least some of the feed stream to the hydrolysis zone, or both.
10. The method of claim 1, wherein the at least one feed stream comprises a first stream containing at least about 90 percent carboxylic acid by weight and a second stream containing at least about 90 percent of a carboxylic acid anhydride by weight.
11. The method of claim 1, wherein the at least one feed stream comprises a stream derived from an esterification process.
12. The method of claim 1, wherein the at least one feed stream comprises a stream derived from a separation process that partially fractionates a mixture of the carboxylic acid and the carboxylic acid anhydride.
13. The method of claim 1, wherein the at least one feed stream comprises a stream derived from a carbonylation process that manufactures the carboxylic acid anhydride.
14. The method of claim 13, wherein the carbonylation process further manufactures the carboxylic acid.
15. The method of claim 6 wherein the at least one feed stream comprises at least about 90 percent acetic acid by weight.
16. The method of claim 1 wherein the at least one feed stream comprises a ratio of the carboxylic acid to the carboxylic acid anhydride in the range of about 60:40 to about 99.5:0.5.
17. The method of claim 1 wherein the at least one feed stream comprises less than about 1 percent by weight of components other than the carboxylic acid and the carboxylic acid anhydride.
18. The method of claim 1 wherein the separated stream comprises in the range of 0.5 to 95 percent of water by weight, wherein the product stream comprises at least 80 percent of carboxylic acid by weight.
19. The method of claim 1 wherein the at least one feed stream comprises at least about 85 percent carboxylic acid by weight, wherein the hydrolysis zone has a temperature in the range of about 20 to about 100° C.
20. The method of claim 1 wherein the stoichiometric excess of water is a ratio of water to carboxylic acid anhydride in the range of about 1.05:1 to about 10:1.

21. The method of claim 1 wherein the vessel comprises a bed or pipe packed with the solid hydrolysis catalyst,
wherein the vessel further comprises a liquid distribution device comprising at least one shower head, spray nozzle, or liquid distribution tray.

22. The method of claim 1 wherein the method further comprises recycling at least some of the separated stream to the hydrolysis zone,
wherein the containment comprises a shell-and-tube heat exchanger,
wherein the separation zone comprises a distillation zone, the separated stream comprises at least one distillation overhead or sidedraw from the distillation zone and the product stream comprises at least one distillation underflow from the distillation zone.

23. The method of claim 1 wherein the method further comprises cooling at least part of the at least one feed stream with a heat exchanger,
wherein the at least one feed stream comprises at least about 85 percent carboxylic acid by weight,
wherein the hydrolysis zone has a temperature in the range of about 20 to about 100° C.,
wherein the at least one feed stream comprises less than about 1 percent by weight of components other than the carboxylic acid and the carboxylic acid anhydride.

24. The method of claim 6 wherein the at least one feed stream comprises at least about 90 percent acetic acid by weight,
wherein the at least one feed stream comprises less than about 1 percent by weight of components other than the acetic acid and the acetic acid anhydride.

25. The method of claim 24 wherein the stoichiometric excess of water is a ratio of water to acetic anhydride in the range of about 1.05:1 to about 1.1:1.

26. The method of claim 7 wherein the at least one feed stream comprises at least about 90 percent acetic acid by weight,
wherein the at least one feed stream comprises less than about 1 percent by weight of components other than the acetic acid and the acetic acid anhydride.

27. The method of claim 26 wherein the stoichiometric excess of water is a ratio of water to acetic anhydride in the range of about 1.05:1 to about 1.1:1.

28. A method comprising:
contacting at least one feed stream comprising a carboxylic acid and a carboxylic acid anhydride with a stoichiometric excess of water in a hydrolysis zone to thereby hydrolyze at least some of the carboxylic acid anhydride, wherein the hydrolysis zone comprises a vessel containing a solid hydrolysis catalyst, wherein the at least one feed stream comprises at least about 40 percent carboxylic acid by weight, wherein the at least one feed stream comprises a ratio of the carboxylic acid to the carboxylic acid anhydride in the range of about 60:40 to about 99.5:0.5;
withdrawing a hydrolyzed stream comprising carboxylic acid and water from the hydrolysis zone; and
processing at least some of the hydrolyzed stream in a separation zone that is not located in the vessel to produce a separated stream comprising carboxylic acid and water and a product stream comprising carboxylic acid;
wherein the at least one feed stream comprises less than about 1 percent by weight of components other than the carboxylic acid and the carboxylic acid anhydride.

29. The method of claim 28 wherein the separated stream comprises in the range of 0.5 to 95 percent of water by weight, wherein the product stream comprises at least 80 percent of carboxylic acid by weight.

30. The method of claim 28 wherein the vessel contains a bed of the solid hydrolysis catalyst.

31. The method of claim 28 wherein the vessel contains a packed bed of the solid hydrolysis catalyst.

32. The method of claim 28 wherein the at least one feed stream comprises at least about 85 percent carboxylic acid by weight,
wherein the hydrolysis zone has a temperature in the range of about 20 to about 100° C.

33. The method of claim 28 wherein the stoichiometric excess of water is a ratio of water to carboxylic acid anhydride in the range of about 1.05:1 to about 10:1.

34. The method of claim 28 wherein the vessel comprises a bed or pipe packed with the solid hydrolysis catalyst,
wherein the vessel further comprises a liquid distribution device comprising at least one shower head, spray nozzle, or liquid distribution tray.

35. The method of claim 28 wherein the method further comprises recycling at least some of the separated stream to the hydrolysis zone,
wherein the hydrolysis zone comprises a shell-and-tube heat exchanger,
wherein the separation zone comprises a distillation zone, the separated stream comprises at least one distillation overhead or sidedraw from the distillation zone and the product stream comprises at least one distillation underflow from the distillation zone.

36. The method of claim 28 wherein the method further comprises cooling at least part of the at least one feed stream to the hydrolysis zone with a heat exchanger,
wherein the at least one feed stream comprises at least about 85 percent carboxylic acid by weight,
wherein the hydrolysis zone has a temperature in the range of about 20 to about 100° C.,
wherein the at least one feed stream comprises less than about 1 percent by weight of components other than the carboxylic acid and the carboxylic acid anhydride.

37. The method of claim 28 wherein the carboxylic acid is acetic acid and the carboxylic acid anhydride is acetic anhydride.

38. The method of claim 37 wherein the stoichiometric excess of water is a ratio of water to acetic anhydride in the range of about 1.05:1 to about 1.1:1.

39. The method of claim 37 wherein the at least one feed stream comprises at least about 90 percent acetic acid by weight,
wherein the at least one feed stream comprises less than about 1 percent by weight of components other than the acetic acid and the acetic acid anhydride.

40. The method of claim 39 wherein the stoichiometric excess of water is a ratio of water to acetic anhydride in the range of about 1.05:1 to about 1.1:1.

41. The method of claim 7 wherein the at least one feed stream comprises at least about 90 percent acetic acid by weight.

42. The method of claim 37 wherein the at least one feed stream comprises at least about 90 percent acetic acid by weight.

* * * * *